US00PP08531P

United States Patent [19]

Bridges

[11] Patent Number: Plant 8,531

[45] Date of Patent: Jan. 11, 1994

[54] MINIATURE ROSE PLANT NAMED 'BRITIDE'

[76] Inventor: Dennis A. Bridges, 2734 Toney Rd., Lawndale, N.C. 28090

[21] Appl. No.: 831,191

[22] Filed: Jan. 31, 1992

[51] Int. Cl.[5] ..... A01H 5/00

[52] U.S. Cl. ..... Plt./7.1

[58] Field of Search ..... Plt. 7.1, 8.1, 11, 14, Plt. 22, 23

*Primary Examiner*—Howard J. Locker
*Assistant Examiner*—E. F. McElwain

[57] ABSTRACT

A new and distinct variety of miniature rose plant characterized by a profusion of off-white blooms. The unusually strong, fragrant exhibition form blooms are held on long stems on a strong plant.

1 Drawing Sheet

BACKGROUND OF THE INVENTION

1. Field of the Invention

The present invention relates to a new and distinct variety of miniature rose plant which has been given the international variety recognition designation "Britide", and is to be marketed in this country under the synonym "Tidewater".

2. Plants Related to the Invention

The plant of this invention was originated as a result of a planned breeding program which had as a seed parent "Jennifer" U.S. Plant Pat. No. 5,857) also of the miniature rose class. While the pollen parent of "Britide" is not known with certitude it was one of a number of selected miniature varieties from which pollen had been taken for crossing with "Jennifer", in the hope of attaining a new plant having some of the better traits of the seed parent and any one of the pollen parent plants involved in the program. Seeds resulting from such crosses were massed, and caused to germinate. Plants resulting were allowed to develop and the progeny were observed in hope of attaining at least one valuable addition to roses of this market class by expressing desired traits which had not been previously seen. The plant of this disclosure is a selection from the progeny of the stated cross(es), and has been asexually reproduced by the taking and rooting of cuttings derived from the plant stems, as performed at Lawndale, N.C. Clones developed in this manner through succeeding propagation are identical to the parent plant in all distinguishing characteristics and establish that "Britide" is stable.

SUMMARY OF THE INVENTION

Among the new and novel characteristics which are possessed by this plant, singly and in combination, which distinguish it from its parents and all other plants of which I am aware are:

1. Blooms of near white are well formed and blemish resistant blooms show exceptional form and substance.
2. Abundant blooms borne singly, and in clusters of up to 5 blooms, on long strong stems.
3. An unusually strong, spicy fragrance.
4. An abundance of semi-glossy, red-mahogany colored new foliage and medium to dark green mature foliage which pleasingly contrasts with and highlights the blooms of off white.

5. Higher than usual disease resistance to common rose diseases, with a higher than usual level of vigor, and growing to a height which is typical of roses of this market class to produce a plant which attractively appoints the home garden while providing cut flowers of exhibition form and quality.

BRIEF DESCRIPTION OF THE DRAWING

The single sheet of the accompanying drawing is a photograph which shows typical specimens of the flowers of the new variety in different stages of development as well as the coloration thereof as accurately as possible in color illustrations of this type.

BOTANICAL DESCRIPTION

The following is a detailed botanical description of my new variety of miniature rose. With color terminology in accordance with The Royal Horticultural Society Colour Chart (R.H.S.C.C.), except where common dictionary terms of color definition are employed.

Type: Hardy, dwarf, bushy, slightly spreading, seedling, greenhouse, outdoors, cut flower, garden decoration, potted plant.
Commercial class: Miniature.
International recognition name: "Britide".
Commercial synonym: "Tidewater".

Flower

Observations were made from specimens grown outdoors at Cleveland County, N.C., U.S.A, In June 1991.
Type: Miniature
Blooming Habit: Continuous
Bud:
*Size*—Large, 2 ½cm in length.
*Form.*—Urn shaped.
*Color.*—When sepals first divide — near white, near to 155B. When petals begin to unfurl — near white, near to 155B. When half-blown — near white, near to 155B.
*Sepals.*—As long as bud, with several pointed appendages
*Peduncle.*—4 ½cm.
*Aspect.*—Has fine red prickles.
*Strength.*—Erect.
*Color.*—Green, near to 146B.
Bloom:
*Size.*—2 ½ inch diameter when fully expanded.

*Borne.*—Usually singly and in cluster of up to 5.

*Form.*—High centered at first, petals loosely rolled outward, becoming flat at maturity.

*Petalage.*—About 36.

*Color.*—During first two days: Inner petals at center of flower. Light yellow, near to 8B. Outer petals: Near to 11D. Base of petals (Point of attachment): Near to 11C. Reverse of petals: Near to 155B with a hint of 36D. General tonality from a distance: off white, near white 155B.

*Color change.*—Blooms continue off-white, near to 155B. General tonality: Off-White, near to 155B. After three or more days: Continued off-white, near to 155B.

Petals:

*Texture.*—Thick appearance: Inside velvety, outside satiny.

*Form.*—Large, Round, high Centered.

*Arrangement.*—Regularly.

*Petaloids in center.*—Medium (8 to 10).

*Persistence.*—Drop off cleanly.

*Fragrance.*—Strong, fruity.

*Lasting quality.*—Long lasting on the plant, 3 to 5 days and and as a cut flower 2 to 3 days.

Reproductive Organs

Stamens, filaments and anthers:

*Arrangement.*—Regularly arranged around styles.

*Color.*—Near to 35B.

Pollen: Color: Yellow, near to 17B.

Styles: Bunches, uneven length, thin.

Stigmas: Color: Near to 155B.

Hips:

*Shape.*—Globular.

*Size.*—1½ to 2 cm.

*Color.*—Green with medium orange shades.

*Seeds.*—Do not protrude

Plant

Form: Slightly spreading.

Growth: Vigorous, uneven branching.

Height attained: 26 to 30 inches.

Foliage: compound of 5 to 7 leaflets.

*Size.*—Medium.

*Quantity.*—Abundant.

*Color.*—New Foliage: Upper side: Near to 183A. Under side: Near to 138D. Old Foliage: Upper side: Near to 147A. Under side: Near to 148B.

*Shape.*—Oval, pointed.

*Texture.*—Upper side: Smooth. Under side: Slightly veined.

*Edge.*—Serrated.

*Serration.*—Slight, even.

*Leaf stem.*—Color: Near to 138A upper side. Near to 138B under side.

*Stipules.*—Medium, 1 cm in length.

*Disease resistance.*—Blackspot, good; Mildew, good: Rust, good.

Wood:

*New wood.*—Smooth bark, near to 147B.

*Old wood.*—Smooth bark, near to 147B.

Thorns:

*Quantity.*—Few on main stalks and laterals.

*Form.*—Flat, oval base.

*Length.*—½cm medium.

*Color when young.*—near to 178B.

Position.—Irregular.

Prickles: Quantity: None.

Winter hardiness: Hardy with little or no die back.

I claim:

1. A new and distinct variety of rose plant of the miniature rose class, substantially as herein shown and described, characterized particularly by an abundance of fragrant blooms of off-white coloration; said blooms being of good substance; firm, thick, petals, borne singly and in clusters, on a slightly spreading plant with semi-glossy, red-mahogany colored new foliage and dark green mature foliage; said plant being easy to propagate from cuttings; and said blooms being long lasting both on the plant and as cut flowers.

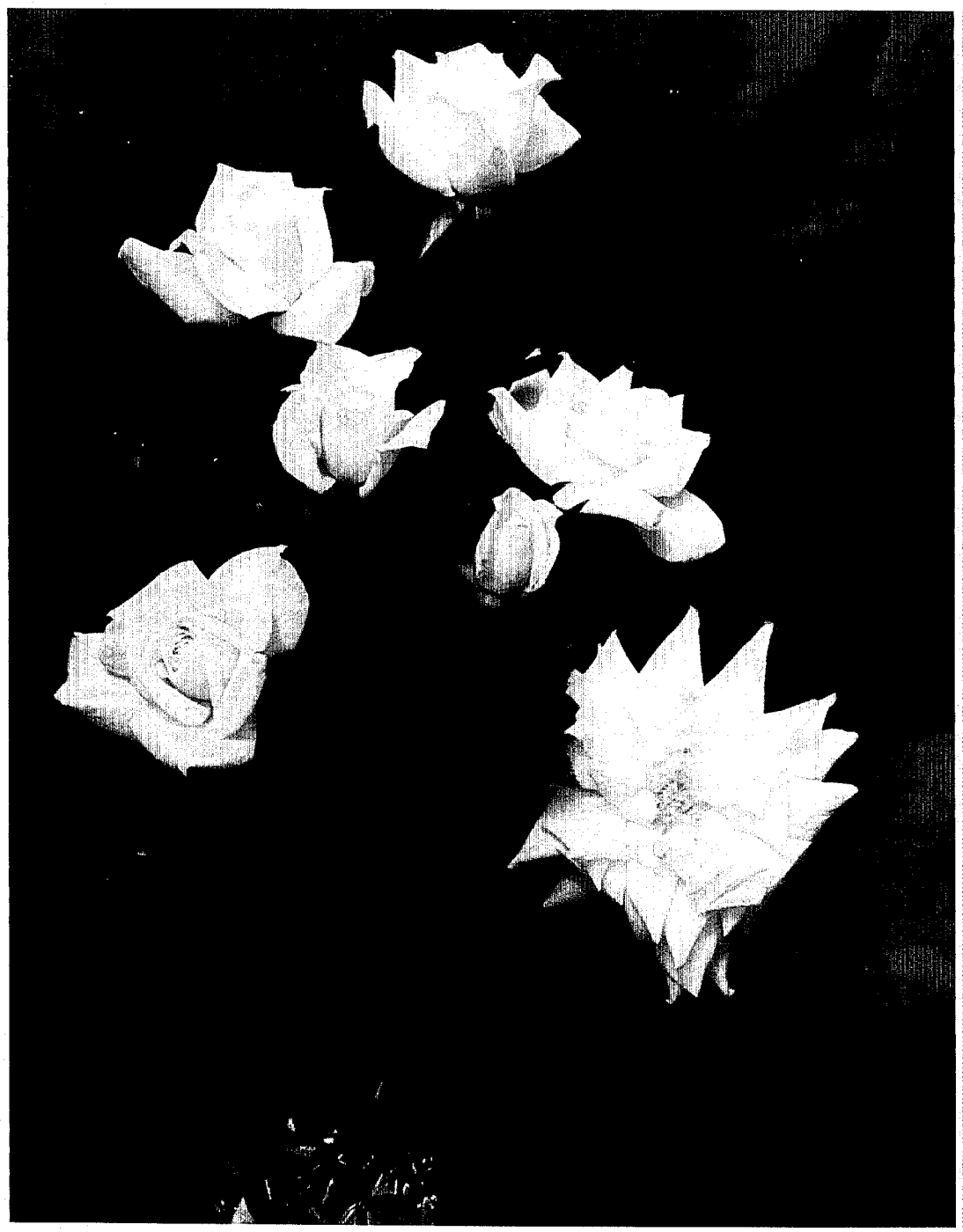

* * * * *